United States Patent [19]
Thomas et al.

[11] Patent Number: 6,077,518
[45] Date of Patent: Jun. 20, 2000

[54] CLONING OF MITE ALLERGENS

[75] Inventors: Wayne Robert Thomas, Nedlands; Geoffrey Alexander Stewart, Leeming; Keven Turner, Dalkeith; Richard John Simpson, Richmond, all of Australia

[73] Assignee: ImmuLogic Pharmaceutical Corporation, Waltham, Mass.

[21] Appl. No.: 08/481,047

[22] Filed: Jun. 7, 1995

Related U.S. Application Data

[62] Division of application No. 08/162,722, Nov. 8, 1993, which is a continuation of application No. 07/458,642, Feb. 13, 1990, abandoned.

[30] Foreign Application Priority Data

Jun. 18, 1987 [AU] Australia .................................. 2523/87
Jun. 17, 1988 [WO] WIPO ...................... PCT/AU88/00195

[51] Int. Cl.[7] .................................................... A61K 39/35
[52] U.S. Cl. .................................... 424/275.1; 424/184.1; 424/185.1; 424/200.1; 435/7.4; 435/69.1; 435/69.3; 435/252.3; 436/826; 530/350; 530/324; 530/325; 530/326; 530/327; 530/328; 530/329

[58] Field of Search .............................. 424/184.1, 185.1, 424/200.1, 275.1; 435/69.1, 69.3, 172.3, 252.3, 320.1; 436/826; 530/350, 324, 325, 326, 327, 328, 329

[56] References Cited

FOREIGN PATENT DOCUMENTS

B3 132771 1/1973 Australia .

OTHER PUBLICATIONS

Stewart et al. (1986) Asian Pacific J. of allergy & Immun, 4(1):71, 1986.
Abstracts from the Annual Meeting (1986) "The physiochemical characterization of a mojor protein allergen from the house dust mite, Dermatophagoides" *Asian Pacific J. of Allergy & Immunol.* 4(1):71 (abstract);.
Chapman et al. "II. MITE ALLERGENS 1. Epitope mapping of mojor dust mite (deratophagoides) allergens using monoclonal antibodies" The UCB Institute of Allergy, MITE ALLERGY A World Wide Problem, Bad Kreuznach, Sep. 1–2, 1987.
Chemical Abstracts vol. 108, p. 148, abstract No. 217095, Chua et al. "Sequence analysis of cDNA coding for a mojor proteases" (1988) abstract.
Chemical Abstracts vol. 105, (1986 p. 552, (abstract No. 189004) Yasaueda, Hiroshi et al. "Isolation and characterization of two allergens from *Dermatophagoides farnae*".
Heymann, et al. (1986) "Antigen Der f 1 from the dust mite *Dermatophagoides farinae*: structural comparison with Der p 1 from *Dermatophagoides pteronyssinus* andepitope specificity of murine lgG and human igE antobodies" *Journal of Immunology* 137:2841–2847;.
Heymann et al. (1986) "Antigen Der f 1 from the dust mite *Dermatophagoides farinae*: Structural Comparison with Der p 1 From *Dermatophagoides pteronyssonis* and Epitope Specificity of Murine lgG and Human lgE Antibodies" *The Journal fo Immunology* 137(9):2841–2847.

K. Y. Chua et al. (1991) "lgE Binging Studies with Large Peptides Expressed From Der p ll c CNA Constructs" *Clinical and Experimental Allergy*, 21:161–166;.
K.Y Chua et al. (1990) "Expression of Dermatophagoides pteronyssinus Allergen, Derp ll, in *Escherichia coli* and the Binding Studies with Human lgE" *Int. Arch Allery Appl. Immunol.* 91:124–129.
Krilis, et al. (1984) "Antigens and allergens from the common house dust mite *Dermatophagoides pteronyssinus*", *Allergy & J. Clin. Immunol.* 74:142–146;.
Lamb, et al. (1988) "The use of nitrocellulose immunoblots for the analysis of antigen recognition by T lymphoctes" *J. of Immunological Methods* 110:1–10;.
Proceedings of the DPC 1st International Symposium on Allergy & Molecular Biology, Apr. 11–12, 1988, Stewart, G. et al. "An Allergen & Antigen Mapping Analysis of a Major Mite Allergen, Der p I" in Laguna Niguel, California;.
Raymond Pierce et al. (1986) "Molecular cloning of Schistosama masoni allergens"BIOCHEM GENETICS 109:191, (abstract No. 143703);.
Stewart, G. "Isolation and Characterization of the Allergen Dpt 12 from *Dermatophagoides pteronyssinus* by Chromatofucusing" Int Arch. Allergy Appl. Immun. 69:224–230;.
Stewart et al (1987) "In Vitro Translation of Messenger RNA from the House Dust Mite *Dermatophagoides pteronyssinus*" *Int Archs Allery Appl. Immun.* 83:384–389.
Stewart et al. (1987) Immunogenicity and Tolerogenicity of a major house dust m ite allergen der p i from Dermatophasgoides pteronyssinus, in Mice and Rats, Int. Archs. Allergy App l. Immun. 83:44–51;.
Stewart et al. (1987) "In Vitro Translation of Messenger RNA from House Dust Mite *Dermatophagoides pteronyssinus*" Int Archs Allergy Appl. Immun. 83:384–359;.
Thomas et al. "4. Expression of the house dust mite allergen der p 1 in E. Coli" The UCB Institute of Allergy, MITE ALLERGY A World–Wide Problem, Bad Kreuznach, Sep. 1–2, 1987.
Thomas et al. (1988) "Cloning and Expression of DNA Coding for the Major House Dust Mite Allergen Der p 1 In *Escherchia coli*" *Int. Archs Appl. Immun.* 85:127–129;.
W.K. Greene et al. (1992) "lgE Binding Structures of the Major House Dust Mite Allergen" *Molecular Immunology* 29(2):257;262;.
Young et al. "Efficient Isolation of Gene by Using Antibody Probes" Proc. Natl. Acad. Sci. USA 80:1194–1198;.

*Primary Examiner*—Laurie Scheiner
*Attorney, Agent, or Firm*—Lahive & Cockfield, LLP; Jane E. Remillard, Esquire; Amy E. Mandragouras, Esq.

[57] ABSTRACT

Isolated allergens of Dermatophagoides (house dust mites) particularly of the species and *Dermatophagoides pteronyssinus*, which are protein allergens or peptides which include at least one epitope of the protein allergen. In addition, the or peptides encoded by the isolated DNA, their use as diagnostic and therapeutic reagents and methods of diagnosing and treating sensitivity to house dust mite allergens.

8 Claims, 10 Drawing Sheets

```
-23
AAA AAC CGA TTT TTG ATG AGT GCA GAA GCT TTT GAA CAC CTC AAA ACT              48
Lys Asn Arg Phe Leu Met Ser Ala Glu Ala Phe Glu His Leu Lys Thr
                        -1   1                     -10

CAA TTC GAT TTG AAT GCT GAA GCT ACT AAC GCC TGC AGT ATC AAT GGA AAT          96
Gln Phe Asp Leu Asn Ala Glu Ala Thr Asn Ala Cys Ser Ile Asn Gly Asn
10                                              20

GCT CCA GCT GPA ATC GAT TTG CGA CAA ATG CGA ACT GTC ACT CCC ATT             144
Ala Pro Ala Glu Ile Asp Leu Arg Gln Met Arg Thr Val Thr Pro Ile
        30                                              40

CGT ATG CAA GGA GGC TGT GGT TCA GCT TTC TCT GGT GTT CTT GCC                 192
Arg Met Gln Gly Gly Cys Gly Ser Ala Phe Ser Gly Val Leu Ala
                        50

GCA ACT GAA TCA GCT TAT TTG CAC CGT AAT CAA CAA TCA GAT CTT                 240
Ala Thr Glu Ser Ala Tyr Leu His Arg Asn Gln Ser Leu Asp Leu
        60                                      70

GCT GAA CAA GAA TTA GTC GAT TGT GCT TCC CAA CAC AAT GGT TGT CAT GGT         288
Ala Glu Gln Glu Leu Val Asp Cys Ala Ser Gln His Asn Gly Cys His Gly
                80

GAT ACC ATT CCA CGT GGT ATT GAA TAC ATC CAA CAT AAT GGT GTC GTC             336
Asp Thr Ile Pro Arg Gly Ile Glu Tyr Ile Gln His Asn Gly Val Val
90                                              100

CAA GAA AGC TAC TAT CGA TAC GTT GCA CGA CAA GAA CGA TCA TGC CGA             384
Gln Glu Ser Tyr Tyr Arg Tyr Val Ala Arg Gln Glu Arg Ser Cys Arg
            110                                         120

CCA AAT GCA CAA CGT TTC GGT ATC TCA AAC TAT TGC CAA ATT TAC CCA             432
Pro Asn Ala Gln Arg Phe Gly Ile Ser Asn Tyr Cys Gln Ile Tyr Pro
                    130
```

Fig. 1A

```
CCA AAT GCA AAC AAA ATT CGT GAA GCT TTG GCT CAA ACC CAC AGC GCT  480
Pro Asn Ala Asn Lys Ile Arg Glu Ala Leu Ala Gln Thr His Ser Ala
        140                             150

ATT GCC GTC ATT ATT GGC ATC ATT GAT TTA GAC GCA TTC CGT CAT TAT  528
Ile Ala Val Ile Ile Gly Ile Ile Asp Leu Asp Ala Phe Arg His Tyr
                    160

GAT GGC CGA ACA ATC ATT CAA CGC GAT AAT GGT TAC CAA CCA AAC TAT  576
Asp Gly Arg Thr Ile Ile Gln Arg Asp Asn Gly Tyr Gln Pro Asn Tyr
170                                     180

CAC GCT GTC AAC ATT GTT GGT TAC AGT AAC GCA CAA GGT GTC GAT TAT  624
His Ala Val Asn Ile Val Gly Tyr Ser Asn Ala Gln Gly Val Asp Tyr
            190                                         200

TGG ATC GTA CGA AAC AGT TGG GAT ACC AAT TGG GAT AAT GGT TAC       672
Trp Ile Val Arg Asn Ser Trp Asp Thr Asn Trp Asp Asn Gly Tyr
                        210

GGT TAT TTT GCT GCC AAC ATC GAT TTG ATG ATG ATT GAA GAA TAT CCA  720
Gly Tyr Phe Ala Ala Asn Ile Asp Leu Met Met Ile Glu Glu Tyr Pro
        220

TAT GTT GTC ATT CTC TAAACAAAAAAGACAATTTCTTATATGATTGTCACTAATTATT  778
Tyr Val Val Ile Leu
        222
TAAATCAAAATTTTTAGAAAATGAATAAATTCATTCACAAAAATTAAAAAAAAAAAAAAAAA
AAAAAAAAAAAAAA 857                                                841
```

Fig. 1B

```
Der p 1  1 Thr Asn Ala Cys Ser Ile Asn - Gly Asn Ala Pro
                 *               *       *
Der f 1  1 Thr Ser Ala Cys Arg Ile Asn Ser Val Asn Val Pro

Der p 1  1 Ala Glu Ile Asp Leu Arg Gln Met
             *       *           *
Der f 1  1 Ser Glu Leu Asp Leu Arg Ser Leu
```

Fig. 3

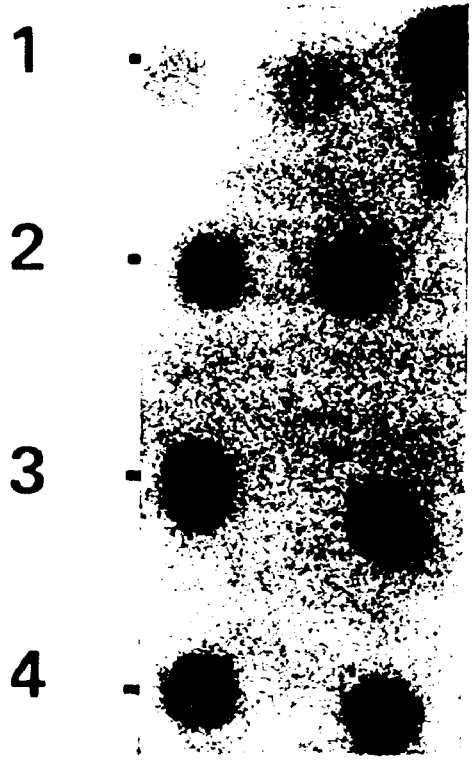
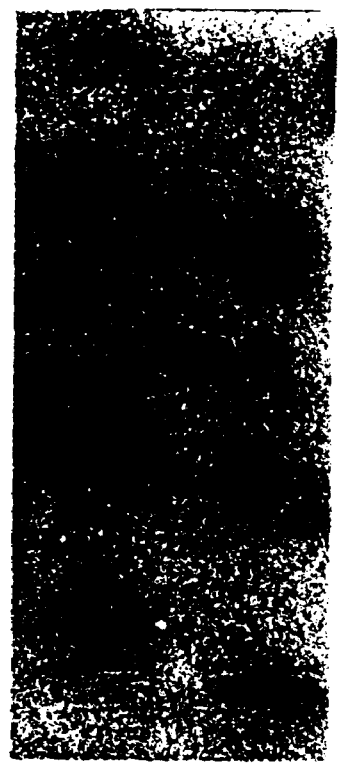
FIG. 5

```
CACAAATTCTTCTTCTTTCCTTACTACTGATCATTAATCTGAAAACAAACCAAACAAACCAT
                        -16                                        -10

TCAAAATGATG TAC AAA ATT TTG TGT CTT TCA TTG TTG GTC GCA GCC GTT
            Met Tyr Lys Ile Leu Cys Leu Ser Leu Leu Val Ala Ala Val
            -1   1                                              10

GCT CGT GAT CAA GTC GAT GTC AAA GAT TGT GCC AAT CAT GAA ATC AAA
Ala Arg Asp Gln Val Asp Val Lys Asp Cys Ala Asn His Glu Ile Lys

AAA GTT TTG GTA CCA GGA TGC CAT GGT TCA GAA CCA TGT ATC ATT CAT
Lys Val Leu Val Pro Gly Cys His Gly Ser Glu Pro Cys Ile Ile His
                    20                                          30

CGT GGT AAA CCA TTC CAA TTG GAA GCC GTT TTC GAA GCC AAC CAA AAC
Arg Gly Lys Pro Phe Gln Leu Glu Ala Val Phe Glu Ala Asn Gln Asn
                            40

ACA AAA ACG GCT AAA ATT GAA ATC AAA GCC TCA ATC GAT GGT TTA GAA
Thr Lys Thr Ala Lys Ile Glu Ile Lys Ala Ser Ile Asp Gly Leu Glu
            50                                          60
```

Fig. 7A

```
GTT GAT GTT CCC GGT ATC GAT CCA AAT GCA TGC CAT TAC ATG AAA TGC
Val Asp Val Pro Gly Ile Asp Pro Asn Ala Cys His Tyr Met Lys Cys
             70                          90

CCA TTG GTT AAA GGA CAA CAA TAT GAT ATT AAA TAT ACA TGG AAT GTT
Pro Leu Val Lys Gly Gln Gln Tyr Asp Ile Lys Tyr Thr Trp Asn Val
         80                                              110

CCG AAA ATT GCA CCA AAA TCT GAA AAT GTT GTC ACT GTT AAA GTT
Pro Lys Ile Ala Pro Lys Ser Glu Asn Val Val Thr Val Lys Val
             100                         120

ATG GGT GAT GAT GGT GTT TTG GCC TGT GCT ATT GCT ACT CAT GCT AAA
Met Gly Asp Asp Gly Val Leu Ala Cys Ala Ile Ala Thr His Ala Lys
                                 129

ATC CGC GAT TAAATCAAACAAAATTTATTGATTTTGTAATCACAAATGATTGATTTTCTT
Ile Arg Asp

TCCAAAAAAAAAAAATAAAATTTTGGGAATTC    581
```

Fig. 7B

Der p II  DQVDVKDCANHEIKKVLVPGCHGSEPCIIHRGKPF

*       * *       *

Der f II  DQVDVKD?ANNEIKKVMVDG?HGSDP?IIHRGKPF

* = NON HOMOLOGOUS RESIDUES.

CLONING OF MITE ALLERGENS

This application is a division of application of Ser. No. 08/162,722 filed on Nov. 8, 1993, , which in turn is a continuation application of Ser. No. 07/458,642 filed on Feb. 13, 1990, abandoned. This application claims priority to PCT/AU88/00195 filed on Jun. 17, 1988 which claims priority to Australian Patent Application No. PI 2523/87 filed on Jun. 18, 1987. The contents of all of the aforementioned application(s) are hereby incorporated by reference.

This invention relates to the cloning of site allergens, in particular it relates to the cloning and expression of DNA coding for house dust mite allergens.

It has long been recognised that the allergy to mites of the genus Dermatophagoides is associated with diseases such as asthma, rhinitis, and atopic dermatitis (13,14). In this regard, the species *D.pteronyssinus* and *D.farinae* predominate and many studies have been performed to identify the allergens they produce. Progress in studying allergy to the house dust mite has been hindered by difficulties in obtaining standardised allergens (1). About 6 antigens elicit most IgE anti-mite antibody responses (2,3) and one of these, *Der p* I, an approx. 27 kDa glycoprotein found in mite faeces reacts with about 80–90% of allergic sera usually as the predominant antigen. Also, because it is a constituent of faeces it is readily airborne and solubilised (4), thus it is presented in a form which is more accessible than allergens in mite bodies.

From 5–10% of people in most populations suffer from asthma, a condition often closely associated with allergy, to the house dust mite, *Dermatophagoides pteronyssinus*. This type of allergy is mediated by, IgE antibodies which react to mite components. The possibility, therefore, exists that desensitisation therapy would be successful for asthma in much the same way as a similar allergy to bee sting can be desensitized by repeated and progressively increased doses of bee venom.

It is therefore one object of the present invention to provide a method for the production of house dust mite allergens, particularly the *Der p* I and *Der p* II allergen, suitable for use in such desensitisation therapy as well as in diagnostic tests for the detection of allergy.

According to the present invention, there is provided a recombinant DNA molecule comprising a nucleotide sequence capable of being expressed as a polypeptide displaying the antigenicity of an allergen of house dust mites of the genus Dermatophagoides, or a peptide comprising at least one epitope thereof, or a nucleotide sequence which hybridizes with such a sequence under conditions of high stringency. In one particular embodiment the nucleotide sequence is capable of being expressed as the major *Der p* I or the *Der p* II allergen of the house dust mite, or a peptide comprising at least one epitope thereof. By way of example, the nucleotide sequence may be characterised as having substantially all or part of the sequence shown in FIG. 1 or FIG. 7.

In work leading to the present invention, recombinant DNA molecules have been constructed comprising nucleotide sequences which code for expression or the Der p I and *Der p* II allergens from *Dermatophagoides pteronyssinus*. The species *Dermatophagoides farinae* and *Dermatophagoides microcerus*, as well as another house dust mite of the same family,*Euroglyphus maynei*, produce similar allergens with antigenic cross reactivity and a high degree of amino acid homology. Thus the present invention extends not only to allergens from *Dermatophagoides pteronyssinus*but also to other mite allergens coded for by DNA which hybridises with its *Dermatophagoides pteronyssinus*counterpart under conditions of high stringency.

In another aspect, this invention provides an expression vector, such as a bacteriophage, containing a nucleotide sequence as described above, and an expression control sequence operatively linked thereto. In addition, this invention provides a host cell containing an expression vector as described above.

In yet another aspect, this invention provides a synthetic protein or polypeptide displaying the antigenicity of all or a portion of an allergen of house dust mites of the genus Dermatophagoides, in particular the major *Der p* I or *Der p* II allergens, or allergens from other house dust mites with antigenic cross-reactivity and a high degree of amino acid homology. Such a synthetic product may comprise a fusion protein comprising a polypeptide component displaying the antigenicity of all or a portion of an allergen of the house dust mite and fused thereto an additional polypeptide, such as β-galactosidase, coded for by the DNA of an expression vector.

A method for the production of a synthetic protein or polypeptide as described above, in particular a fusion protein as described, comprises the steps of culturing a host cell containing an expression vector as described, and recovering the synthetic protein or polypeptide from the culture.

The term "synthetic" as used herein relates to proteins or polypeptides produced by cloning and expression of a nucleotide sequence as described herein.

The synthetic proteins or polypeptides or "synthetic allergens" produced in accordance with this invention display the antigenicity of the native allergen. By way of example, a cDNA clone coding for the major allergen *Der p* I produces a fusion protein which reacts with rabbit anti-*Der p* I antiserum. Accordingly, such a fusion protein has potential for use as an antigenic component in diagnostic tests and therapeutic (for example desensitisation) compositions and treatments.

In particular, the synthetic allergens may be used as in vitro and in vivo diagnostic reagents as demonstrated by their antigenic similarity with the native mite allergens and their ability to react with IgE from serum of people with allergy to mites. Further, they may be used as therapeutic substances by desensitisation as demonstrated by the ability of synthetic *Der p* I to inhibit IgE responses of mice to mature *Der p* I.

Further features of the present invention will be apparent from the following Example which is included by way of illustration of the invention. In the drawings:

FIG. 1 shows the nucleotide and predicted amino acid sequence of cDNA λgt 11 p1(13T). Numbers to the right are nucleotide positions whereas numbers above the sequence are amino acid positions. Positive amino acid residue numbers correspond to the sequence of the mature excreted *Der p* I beginning with threonine. Negative sequence numbers refer to the proposed transient pre- and preproenzyme forms of *Der p* I. The arrows indicate the beginning of the proposed proenzyme sequence and the mature *Der p* I, respectively. Residues -15 to -13 enclosed by an open box make up the proposed cleavage for the proenzyme formation, and the dashed residues 52-54 represent a potential N-glycosylation site. The termination TAA codon and the adjacent polyadenylation signal are underlined. Amino acid residues 1-41, 79-95, 111-142, and 162-179 correspond to known tryptic peptide sequences determined by conventional amino acid sequencing analysis.

FIG. 3 is a comparison of N-terminal sequences of *Der p* I and *Der f* I. The amino acid sequence for *Der p* I is equivalent to amino acids 1-20 in FIG. 1; the *Der f* I sequence is from reference (12).

Figure 4:
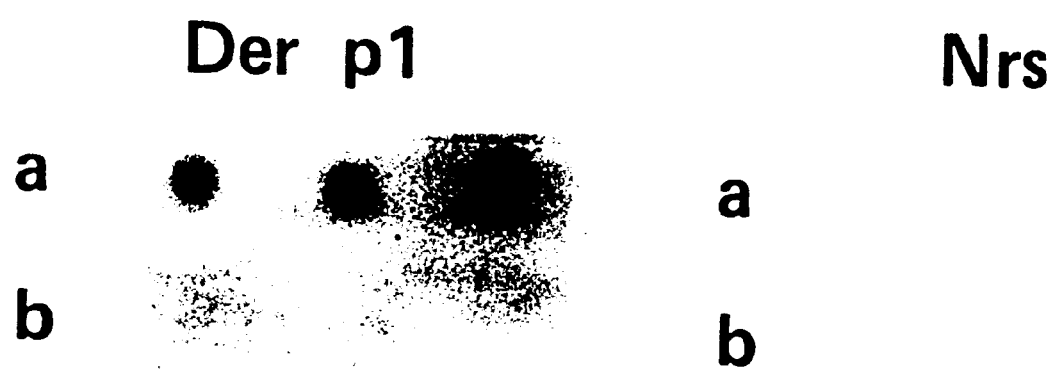

FIG. 4 shows the reactivity of λgt11 p1(13T) with anti *Der p* 1. Lysates from Y1089 lysogens induced for phage were reacted by dot-blot with rabbit anti-*Der p* 1 (Der p I) or normal rabbit serum (Nrs). Dots (2 µl) were made in triplicate from lysates of bacteria infected with λgt11 p1(13T) (a) or λgt11 (b). When developed with $^{125}$I-protein A and autoradiography only the reaction between λgt11 p1(13T) lysate and the anti-*Der p* 1 showed reactivity.

FIG. 5 shows reaction of clone pGEX-p1(13T) with IgE in allergic serum. Overnight cultures of pGEX or pGEX-p1 where diluted 1/10 in broth and grown for 2 hours at 37°. They were induced with IPTG, grown for 2 hours at 37°. The bacteria were pelletted and resuspended in PBS to 1/10 the volume of culture media. The bacteria were lysed by freeze/thaw and sonication. A radioimmune dot-blot was performed with 2 µl of these lysates using mite-allergic or non-allergic serum. The dots in row 1 were from *E.coli* containing pGEX and row 2-4 from different cultures of *E.coli* infected with pGEX-p1(13T). Reactivity to pGEX-p1 (13T) was found with IgE in allergic but not non-allergic serum. No reactivity to the vector control or with non-allergic serum was found.

Figure 6:
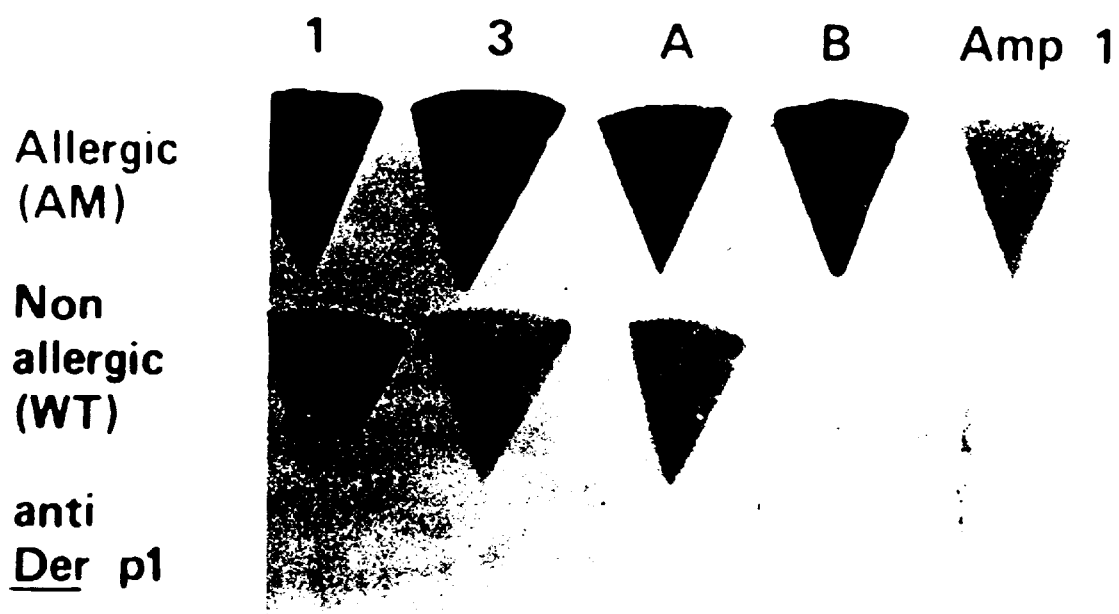

FIG. 6 shows seroreactivity of cDNA clones coding for *Der p* II in plaque radioimmune assay. Segments of nitrocellulose filters from plaque lifts were taken from clones 1, 3, A, B and the vector control Ampl. These were reached by immunoassay for human IgE against allergic serum (AM) in row 1, non-allergic serum (WT) in row 2 and by protein A immunoassay for *Der p* I with rabbit antiserum in row 3. The clones 1, 3 and B reacted strongly with allergic serum but not non-allergic or vector control. (Clone B and vector control were not tested with non-allergic serum).

FIG. 7 shows the nucleotide and predicted amino acid sequence of cDNA of λgt11 p II (Cl). Numbers to the right are nucleotide positions and numbers above are amino acid positions. Positive numbers for amino acids begin at the known N-terminal of *Der p* II and match the known sequence of the first 40 residues. Residues -1 to -16 resemble a typical leader sequence with a hydrophobic core.

FIG. 8 shows the N-terminal amino acid homology of *Der p* II and *Der f* II. (*Der f* II sequence from reference 30.)

EXAMPLE 1

Materials and Methods

Cloning and Expression of cDNA.

Polyadenylated mRNA was isolated from the mite *Dermatophagoides pteronyssinus* cultured by Commonwealth Serum Laboratories, Parkville, Australia, and cDNA was synthesised by the RNA-ase H method (5) using a kit (Amersham, International, Bucks). After the addition of EcoRI linkers the cDNA was ligated into λgt11 and plated in *E.coli* Y1090 (r-) (Promega Biotec, Madison, Wis.), to produce a library of 5×10$^5$ recombinants. Screening was performed by plaque radioimmune assay (6) using a rabbit anti-*Der p* 1 antiserum (7). Reactivity was detected by developing with $^{125}$I-Staphyloccocal protein A and autoradiography (8). Phage producing plaques reactive with the antiserum were checked for the ability of their DNA to hybridise with 17-mer oligonucleotides constructed on the basis of amino acid sequences obtained from three tryptic peptides obtained from faecal *Der p* 1 (17).

In brief, *Der p* 1 was isolated by gel filtration, chromatofocusing and fast liquid protein chromatography on a TSK 3000 SW column and then high performance reversed-phase liquid chromatography. Reduction, carboxymethlation and tryptic digestion were performed by standard techniques (9) and peptides were isolated by HPLC using a Brownlee Bu-300 column and a linear gradient of 0–60% A-B where A was 10 mM KH$_2$PO$_4$ pH 6.5, and B was acetonitrile. Amino acid sequences were determined on an Applied Biosystems (Model 470A) gas phase sequencer (9). Oligonucleotides were synthesised using an Applied Biosystem model 370A synthesiser and purified by reversed-phase HPLC. For hybridisation, oligonucleotides were labelled by polynucleotide kinase (Promega Biotec) using 20 pmole of DNA and 20 pmole γ-32P-ATP at 1400 Ci/mmole (10). Labelled oligonucleotides were purified by 15% polyacrylamide gel electrophoresis. Plaques were lifted onto nitrocellulose (Schleicher and Schull, Dassel, West Germany) and denatured and baked (10). Hybridisations were performed overnight in 6× sodium chloride sodium citrate pH 7 (SSC) (10), 0.1% SDS at 37° at 10$^6$ cpm/ml and washed for 1 hr. at 37° C. in 6×SSC containing 0.1% Triton X-100.

Isolation of Genomic DNA.

Extraction of mite genomic DNA was carried out by a modified guanidium-HCl/cesium chloride (CsCl) method (15). 10 g of live mites were ground in the presence of liquid nitrogen and sand to form a paste. 8 ml of 6 M guanidine hydrochloride in 0.1 M sodium acetate buffer pH 5.2 were then added and the mixture was homogenized and spun at 10,000 rpm for 30 min in a Sorval SS34 rotor. The supernatant was collected and layered onto a CsCl pad (5ml of 4.8 M CsCl in 10 mM EDTA) and centrifuged at 37,000 rpm for 16 h at 15° C. in a SW41 T1 rotor (Beckman Instruments, Inc., Fullerton, Calif.). The DNA band at the interphase was collected and diluted 1:15 in 10 mM Tris HCl/1 mM EDTA buffer, pH 8.0. Banding of genomic DNA in CsCl was carried out by the standard method.

Isolation of DNA from λgt11 p1 cDNA Clone.

Phage DNA from λgt11 p1 clone was prepared by a rapid isolation procedure. Clarified phage plate lysate (1 ml) was mixed with 270 µl of 25% wt/vol polyethylene glycol (PEG 6000) in 2.5 N NaCl and incubated at room temperature for 15 min. The mixture was then spun for 5 min in a microfuge (Eppendorf, Federal Republic of Germany), and the supernatant was removed. The pellet was dissolved in 100 µl of 10 mM Tris/HCl pH 8.0 containing 1 mM EDTA and 100 mM NaCl. This DNA preparation was extracted 3 times with phenol/chloroform (1:1) and the DNA was precipitated by ethanol.

DNA Hybridization.

Nucleic acid was radiolabelled with $^{32}$P by nick translation (10). DNA samples were digested with appropriate restriction enzymes using conditions recommended by the supplier. Southern blots were prepared using Zeta-Probe membranes (Bio-Rad Laboratories, Richmond, Calif.). Prehybridization, hybridization, posthybridization washes were carried out according to the manufacturers recommendations (bulletin 1234, Bio-Rad Laboratories).— Specifically, the following conditions were used:

Prehybridization:

| | |
|---|---|
| 1.5 ml distilled water | |
| 5.0 ml deionized formamide | 50% formamide |
| 2.0 ml 20 × SSPE | 4 × SSPE |
| 0.5 ml 20% SDS | 1% SDS |
| 0.5 ml 10% BLOTTO | 0.5% BLOTTO |
| *0.5 ml 10 mg/ml salmon sperm DNA | 0.5 mg/ml carrier DNA |

*Prehybridization temperature: 43° C.

Hybridization:

| 1.4 ml distilled water | |
| --- | --- |
| 5.0 ml deionized formamide | 50% formamide |
| 2.0 ml 20 × SSPE | 4 × SSPE |
| 0.5 ml 20% SDS | 1% SDS |
| 0.5 ml 10% BLOTTO | 0.5% BLOTTO |

Hybridization temperature: 43° C.
Criterion (difference between Tm and hybridization temperature): 20° C.
Washing At no stage were the membranes be permitted to dry.

At the completion of hybridization, membranes were removed from their hybridization bags into 2× SSC, rinsed briefly, then washed successively by vigorous agitation for 15 minutes at room temperature in the following solutions (using approximately 50 ml/mini-gel membrane):

| 2 × SSC/0.1% SDS |
| --- |
| 0.5 × SSC/0.1% SDS |
| 0.1 × SSC/0.1% SDS |

The final wash was performed for 30 minutes in pre-warmed 0.1×SSC/1% SDS at 50° C. or (i.e., approximately 10–15°C. below the Tm).
Cloning and DNA Sequencing.

To clone the 0.8-kb cDNA insert from clone λgt11 p 1 into plasmid pUC8, phage DNA was digested with EcoRI restriction enzyme and then ligated to EcoRI-digested pUC8 DNA and used to transform *Escherichia coli* JM83. The resulting recombinant plasmid was designated as pHDM 1.

Figure 2:
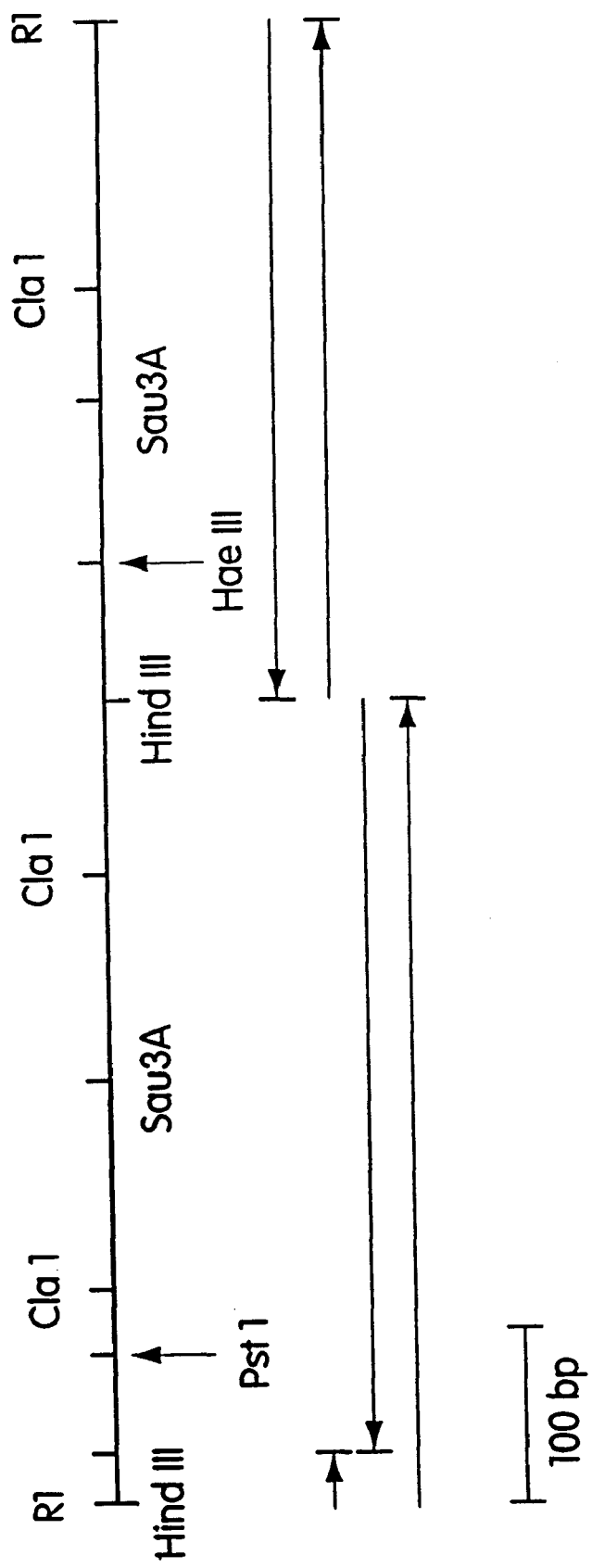
FIG. 2 shows the restriction map of the cDNA insert of clone λgt11 p1(13T) and the strategy of DNA sequencing. Arrows indicate directions in which sequences were read.

To obtain clones for DNA sequence analysis, the cDNA insert was isolated from pHDM 1 and ligated to M13-derived sequencing vectors mp18 and mp19 (16). Transformation was carried out using *E.coli* JM107 and sequencing was performed by the dideoxynucleotide chain termination method (11).
Results Several phage clones reacted with the rabbit anti *Der p* I serum and hybridised with all 3 oligonucleotide probes. One of these, λgt11 p1(13T), was examined further. The nucleotide sequence of the cDNA insert from this clone, λgt11 p 1, was determined using the sequencing strategy shown in FIG. 2. The complete sequence was shown to be 857 bases long and included a 69-base-long 5' proximal end sequence, a coding region for the entire native *Der p* I protein of 222 amino acids with a derived molecular weight of 25,371, an 89-base-long 3' noncoding region and a poly (A) tail of 33 residues (FIG. 1).

The assignment of threonine residue at position 1 as the NH$_2$-terminal amino acid of *Der p* I was based on data obtained by NH$_2$-terminal amino acid sequencing of the pure protein isolated from mite excretions (17). The predicted amino acid sequence matched with data obtained by amino acid sequence analysis of the NH$_2$-terminal region as well as with internal sequences derived from analyses of tryptic peptides (FIG. 1). The complete mature protein is coded by a single open reading frame terminating at the TAA stop codon at nucleotide position 736-738. At present, it is not certain whether the first ATG codon at nucleotide position 16-18 is the translation initiation site, since the immediate flanking sequence of this ATG codon (TTGATGA) showed no homology with the Kozak consenses sequence (ACCATGG) for the eukaryotic translation initiation sites (18). In addition, the 5' proximal end sequence does not code for a typical signal peptide sequence (see below).

The amino acid sequence predicted by nucleotide analysis is shown in FIG. 1. A protein data-base search revealed that the *Der p* I amino acid sequence showed homology with a group of cysteine proteases. Previous cDNA studies have shown that lysosomal cathepsins B, a mouse macrophage protease and a cysteine protease from an amoeba have transient pre- and proform intermediates (19-21), and inspection of the amino acid sequence at the 5' proximal end of the λgt11 p1 cDNA clone suggests that *Der p* I may be similar. First, the hydrophilicity plot (22) of the sequence preceding the mature protein sequence lacks the characteristic hydrophobic region of a signal peptide (23) and second, an Ala-X-Ala sequence, the most frequent sequence preceding the signal peptidase cleavage site (24,25), is present at positions -13, -14, -15 (FIG. 1). Therefore, it is proposed that cleavage between pro-*Der p* I sequence and the pre-*Der p* I sequence occurs between Ala (-13) and Phe (-12). Thus, pro-*Der p* I sequence begins at residues Phe (-12) and ends at residues Glu (-1). The amino acids residues numbered -13 to -23 would then correspond to a partial signal peptide sequence.

When the 857-bp cDNA insert was radiolabelled and hybridized against a Southern blot of EcoRI-digested genomic DNA from house dust mite, hybridization to bands of 1.5, 0.5, and 0.35 kb was observed (data not shown). As shown in the restriction enzyme map of the cDNA insert (FIG. 2), there was no internal EcoRI site and the multiple hybridization bands observed suggest that *Der p* I is coded by a noncontiguous gene. The results also showed little evidence of gene duplication since hybridization was restricted to fragments with a total length of 2.4 kb.

The N-terminal can be compared with N-terminal of the equivalent protein from *D.farinae* (*Der f* 1) (12). There is identity in 11/20 positions of the sequences available for comparison (FIG. 3).

To examine the protein produced by λgt11 p1(13T), phage was lysogenised in Y1089 (r-) and the bacteria grown in broth culture at 30°. Phage was induced by temperature switch and isopropyl thiogalactopyranoside (IPTG) (6) and the bacteria were suspended in PBS to 1/20 of the culture volume, and sonicated for an antigen preparation. When examined by 7.5% SDS-PAGE electrophoresis it was found that λgt11 p1(13T) did not produce a Mr 116K β-galactosidase band but instead produced a 140K band consistent with a fusion protein with the *Der p* I contributing a 24 kDa moiety (6). Rabbit anti *Der p* I was shown to react with the lysate from λgt11 p1(13T) (FIG. 4).

EXAMPLE 2

Expression of *Der p* I cDNA products reactive with IgE from allergic serum.

The DNA insert from λgt11 p1(13T) which codes for *Der p* I was subcloned into the EcoRI site of the plasmid expression vector (pGEX)(26) where it could be expressed as a fusion with a glutathione transferase molecule. *E.coli* infected with this plasmid pGEX-p1(13T) or with the vector alone were grown to a log phase culture and harvested by centrifugation. The bacteria were suspended in PBS to 1/20 of their culture volume and lysed by freeze-thawing. The lysate was shown by sodium didodecyl-sulphate polyacrylamide electrophoresis to express a fusion protein in high concentration of the expected Mr 50,000. These lysates were then tested for their ability to react with IgE from allergic serum by radioimmune dot-blot conducted by the method described by Thomas and Rossi (27). The serum was taken from donors known to be mite-allergic or from non-allergic controls. Reactivity was developed by $^{125}$I-monoclonal anti-IgE and autoradiography. FIG. 5 shows the lysate from pGEX-p1(13T), but not the vector control reacted with IgE in allergic serum, but not non allergic serum.

EXAMPLE 3

Inhibition of IgE antibody responses to Der p I by treatment with the product from a cDNA clone coding for Der p I.

E.coli lysogenised by λgt11 p1(13T) were grown and induced by tempereature switch to produce a recombinant fusion protein which was consistent with a 24 kd Der p I moiety and a 116 kd β-galactosidase moiety (p1(13T) (28).

This protein was mostly insoluble and could be isolated to about 90% purity, judged by sodium didodecyl polyacrylamide electrophoresis, by differential centrifugation. A similar protein was produced from another gt11 cDNA mite clone λgt pX (2c). To test for the ability of the recombinant protein to modify IgE antibody responses to Der p I, groups of 4–5 CBA mice were injected intraperitoneally with 2mg of the p1 (13T) or pX (2c) fusion proteins and after 2 days given a subcutaneous injection of 5μg of native Der p I (from mite culture medium) in aluminium hydroxide gel. The IgE antibody titres were measured by passive cutaneous anaphylaxis (PCA) after 3 and 6 weeks. The methods and background data for these responses have been described by Stewart and Holt (29). For a specificity control, groups of mice injected with p1(13T) or pX (2c) were also injected with 10 μg of ovalbumin in alum. Responses were compared to mice without prior p1(13T) or pX (2c) treatment (Table 1). After 3 weeks mice either not given an injection of recombinant protein or injected with the control pX (2c) had detectable anti Der p I PCA titres (½ or greater). Only 1/5 of mice treated with recombinant p1(13T) had a detectable titre and this at 1/4 was lower than all of the titres of both control groups. Titres of all groups at 6 weeks were low or absent (not shown). The PCA response to ovalbumin was not significantly affected by treatment with recombinant proteins. These data show the potential of the recombinant proteins to specifically decrease IgE responses as required for a desensitising agent.

TABLE 1

Inhibition of anti Derp I IgE by preinjection with recombinant Derp I.

| group | preinjection −2 days | immunising injection (d0) (5μg/alum) | IgE (PCA) titres at d21 responders | titres |
|---|---|---|---|---|
| 1 | — | Derp I | 4/4 | 1/16–1/64 |
| 2 | pX(2C) | Derp I | 5/5 | 1/8–1/16 |
| 3 | p1(13T) | Derp I | 1/5* | 1/4* |
| 4 | — | ovalbumin | 4/4 | 1/64–1/256 |
| 5 | pX(2C) | ovalbumin | 5/5 | 1/32–1/128 |
| 6 | p1(13T) | ovalbumin | 5/5 | 1/64–1/256 |

Mice were given a preinjection on day −2 and then immunised with Derp I or ovalbumin on day 0. Serum antibody titres were measured on day 21 and 42 by PCA in rat skin. Significant anti Derp I titres were not detected on day 42 (not shown). The PCA were measured to Derp I for groups 1–3 and ovalbumin for groups 4–6. The anti Derp I titres were lower (p < 0.001)* when pretreated with recombinant Derp I p1(13T).
*Mann Whitney analysis.

EXAMPLE 4

Expression of Der p I antigenic determinants by fragments of the cDNA from λgt11 p1(13T)

The cDNA from λgt11 (13T) coding for Der p I was fragmented by sonication. The fragments (in varying size ranges) were isolated by electrophoresis, filled in by the Klenow reaction to create blunt ends. EcoRI linkers were attached and the fragment libraries cloned in λgt11. The methods used for the fragments cloning were the same as that used for cDNA cloning (6). Plaque immunoassay was used for screening with rabbit anti Der p I. Three phage clones reacting with the antiserum were isolated and the oligonucleotide sequences of the cloned fragments obtained. Two of these were found to code for Der p I amino acids 17–55 (see FIG. 1 for numbering) and one for amino acids 70–100. Such fragments will eventually be useful for both diagnostic reagents to determine epitope reactivity and for therapy where molecules of limited allergenicity may increase safety of desensitisation.

EXAMPLE 5

Cloning and expression of cDNA coding for the major mite allergen Der p II.

The Dermatophagoides pteronyssinus cDNA library in λgt11 previously described was screened by plaque radio-immune assay using nitrocellulose lifts (6). Instead of using specific antisera the sera used was from a person allergic to house dust mites. The serum (at ½ dilution) was absorbed with E.coli. To detect reactivity an $^{125}$I labelled monoclonal anti IgE was used (at 30 ng/ml with 2×10$^6$ cpm/ml (approx.30% counting efficiency)). After 1 hour the filters were washed and autoradiography performed. Using this procedure 4 clones reacting with human IgE were isolated. It was found they were related by DNA hybridisation and had an identical pattern of reactivity against a panel of allergic sera. FIG. 6 shows IgE reactivity in plaque radio-immunoassay against allergic serum (AM) (top row) or non allergic (WT). Here clones 1, 3 and 8 react strongly, but only against allergic sera. The amp 1 segments (present in row 1) are a λgt11 vector control. The bottom row is an immunoassay with rabbit anti Der p I, 125 developed by I staphylococcus protein A which shows no significant reactivity. The clones were tested against a panel of sera. Serum from five patients without allergy to mite did not react, but serum from 14/17 people with mite allergy showed reactivity. The DNA insert from the clone λgt11 pII(Cl) was subcloned into M13 mp18 and M13 mp19 and sequenced by the chain termination method. The nucleotide sequence (FIG. 7) showed this allergen was Der p II by (a) The homology of the inferred amino acid sequence of residue 1-40 with that of the N-terminal amino acid of Der o II (30) and (b) the homology of this sequence with the equivalent Der f II allergen from Dermatophagoides farinae (30).

REFERENCES

1. Ford, A. W., Rawle, F. C., Lind, P., Spieksma, F. T. M., Lowenstein, H., Platts-Mills, T. A. E. (1985). Standardisation of Dermatophagoides pteronyssinus. Assessment of potency and allergen content in the coded extracts. Int.Arch.Allergy Appl.Immunol. 1 : 58–67.
2. Lind, P., Lowenstein, H. (1983). Identification of allergens in Dermatophagoides pteronyssinus mite body extract by crossed radioimmunelectrophoresis with two different rabbit antibody pools. Scand.J. Immunol. 17 : 263–273.
3. Krilis, S., Baldo, B. A., Basten, A. (1984) Antigens and allergens from the common house dust mite Dermatophagoides pteronyssinus Part II. Identification of the major IgE binding antigens by crossed radioimmunoelectrophoresis. *J.Allergy Clin.Immunol.* 74 : 142–146.
4. Tovey, E. R., Chapman, M. D., Platts-Mills, T. A. E. (1981). Mite faeces are a major source of house dust allergens. *Nature* 289 : 592–593.
5. Gubler, U., Hoffman, B. J. (1983) A simple and very efficient method for generating cDNA libraries. *Gene* 25 : 263–269.
6. Huynh, T. V., Young, R. A., Davis, R. W. Constructing and screening cDNA libraries in λ10 and λgt11 . p48–78 in DNA Cloning Col.1, A practical approach. Ed. D. M. Glover, IRL press.
7. Stewart, G. A., Thomas, W. R. (1987). In vitro translation of messenger RNA from the house mite *Dermatophagoides pteronyssinus*. *Int.Arch.Allergy Appl.Immunol.* 83:384–389.
8. Thomas, W. R., Rossi, A. A. (1986) Molecular cloning of DNA coding for outer membrane proteins of *Haemophilus influenzae* type b. *Infection and Immunity.* 52 : 812–817.
9. Simpson, R. J., Smith, J. A., Mortiz, R. L., O'Hare, M. J., Rudland, P. S., Morrison, J. R., Lloyd, C. J., Grego, B., Burgess, A. W. and Nice, E. L. (1985) Rat Epidermal Growth Factor : Complete amino acid sequence. *Eur.J-.Biochem.* 153 : 629–637.
10. Maniatis, T., Fritsch, E. F., Sambrook, J. (1982) Molecular cloning. A Laboratory Manual, Cold Spring Harbor Laboratory,.
11. Sanger, F., Nicklen, S., Coulson, A. R.(1977). DNA sequencing with chain-terminating inhibitors. *Proc.Nat-l.Acad.Sci.* 74 : 5463–5467.
12. Heyman, P. W., Chapman, M. D., Platts-Mills, T. A. E. (1986) Antigen *Der f* 1 from the house dust mite *Dermatophagoides farinae* : structural comparison with *Der p* 1 from *Dermatophagoides pteronyssinus* and epitope specificity of murine IgG and human IgE antibodies. *J.Immunol.* 137 : 2841–2847.
13. Voorhorst, R., Spieksma-Boezeman, M. I. A., and Spieksma, F. Th. M. (1964). Is a mite (Dermatophagoides sp) the producer of the house dust allergen. *Allerg.Asthma.* 10:329.
14. Voorhorst, R., Spieksma, F. Th. M., Varekamp, H., Leupen, M. J. and Lyklema, A. W., (1967). The house dust mite (*Dermatophagoides pteronyssinus*) and the allergens it produces. Identity with the house dust allergen. *J.Allergy.* 39:325.
15. Stewart, G. A. and Thomas, W. R. (1987). In vitro translation of messenger RNA from the house dust mite *Dermatophagoides pteronyssinus*. *Int.Arch.Allergy Appl.Immunol.* 83:384.
16. Messing, J. (1983). New M13 vectors for cloning. Methods Enzymol. 101:20.
17. Stewart, G. A., Simpson, R. J., Thomas, W. R. and Turner, K. J. (1986). The physicochemical characterisation of a major protein allergen from the house dust mite, EP. *Asian Pac.J. Allergy, Immunol.* 5:71.
18. Kozak, M. (1984). Compilation and analysis of sequences upstream from the translational start site in eukaryotic mRNAs. *Nucleic.Acids Res.* 12:857.
19. San Sequndo, B., Chain, S. J. and Steiner, D. F. (1985). Identification of cDNA clones encoding a precursor of rat liver cathepsin B. *Proc.Natl.Acad.Sci. USA.* 82:2320.
20. Portnoy, D. A., Erickson, A. H., Kochan, J., Ravetch, J. V. and Unkeless, J. C. (1986). Cloning and characterization of a mouse cysteine proteinase. *J.Biol.Chem.* 1:14697.
21. Williams, J. G., North, M. J. and Mahbubani, H. (1985). A developmentally regulated cysteine proteinase in *Dictyostelium discoideum*. *EMBO (Eur.Mol.Biol.Organ.)J.* 4:999.
22. Hopp, T. P. (1986). Protein surface analysis. Method for identifying antigenic determinants and other interaction sites. *J.Immunol.Methods.* 88:1.
23. Von Heijne, G. (1984). Analysis of the distribution of charged residues in the N-terminal region of signal sequences: implications of protein export in prokaryotic and eukaryotic cells. *EMBO (Eur.Mol.Biol.Organ.)J.* 3:2315.
24. Ullrich, A., Shine, J., Chirgwin, J., Pictet, R., Tischer, E., Rutter, W. J. and Goodman, H. W. (1977). Rat insulin genes: Construction of plasmids containing th coding sequences. *Science (Wash.DC)* 196:1313.
25. Carne, T. and Scheele, G. (1985). Cell Biology of the Secretory Process. M. Cantin, editor. S. Karger A G, Basel. 73.
26. Smith, D. and Johnson (1988), *Gene* (in press).
27. Thomas, W. R. and Rossi, A. A. (1986). Molecular cloning of DNA coding for outer membrane proteins of *Haemophilus influenzae* Type b. *Infection and Immunity* 52:812–817.
28. Thomas, W. R., Stewart, G. A., Simpson, R. J., Chua, K. Y., Plozza, T. M., Dilworth, Dr. U., Nisbet, A. and Turner, K. J. (1987). Cloning and expression of DNA coding for the major house dust mite allergen *Der p* I in *Escherichia coli*. *Int.Arch.Allergy Appl.Immunol.* 85:127–129.
29. Stewart, G. A. and Holt, P. G. (1987). Immunogenicity and tolerogenicity of a major house dust mite allergen *Der p* I. *Int.Arch. Allergy Appl Immunol.* 83: 44–51.
31. Chapman, M. D., Heymann, P. W. and Platts-Mills, T. A. E. (1987). Mite allergens 1. Epitope mapping of major dust mite (Dermatophagoides) allergens using monoclonal antibodies. Mite Allergy—A World Wide Problem. Ed. A. L. deWeck and A. Todt. The UCB Institute of Allergy.

We claim:

1. An isolated peptide from a *Der p* I protein allergen having the amino acid sequence shown in FIG. 1, wherein said peptide (a) comprises at least one epitope of said *Der p* I protein allergen; (b) is produced recombinantly or synthetically; (c) is free of all native dust mite proteins and peptides; and (d) does not comprise the entire amino acid sequence shown in FIG. 1.

2. A therapeutic composition comprising a peptide of claim 1 and a pharmaceutically acceptable carrier.

3. A method of treating sensitivity in an individual to house dust mites, comprising administering to the individual a composition of claim 2 in an amount sufficient to desensitize the individual to a protein allergen of Dermatophagoides.

4. A diagnostic composition comprising an isolated peptide of claim 1.

5. An isolated peptide from a protein allergen of Dermatophagoides, wherein said peptide (a) comprises at least one epitope of said protein allergen; (b) is encoded by a nucleic acid which hybridizes under conditions of high stringency to a portion of the nucleotide sequence shown in FIG. 1 or the complementary nucleotide sequence, wherein said high stringency conditions comprise hybridization at Tm-20 followed by at least one post-hybridization wash at Tm-12 (c) is produced recombinantly or synthetically; (d) is free of all native dust mite proteins and peptides; and (e) does not comprise the entire amino acid sequence shown in FIG. 1.

6. A therapeutic composition comprising an isolated peptide of claim 5 and a pharmaceutically acceptable carrier.

7. A method of treating sensitivity in an individual to house dust mites, comprising administering to the individual a therapeutically effective amount of a composition of claim 6.

8. A diagnostic composition comprising an isolated peptide of claim 5.

* * * * *

UNITED STATES PATENT AND TRADEMARK OFFICE
CERTIFICATE OF CORRECTION

PATENT NO. : 6,077,518
DATED : June 20, 2000
INVENTOR(S) : Wayne R. Thomas, et al.

It is certified that error appears in the above-identified patent and that said Letters Patent is hereby corrected as shown below:

On the cover page: After [75] Inventors, delete "Keven Turner, Dalkeith", and insert -- KEVIN J. TURNER, CRAWLEY --.

Signed and Sealed this

Twenty-second Day of May, 2001

Attest:

NICHOLAS P. GODICI

Attesting Officer        Acting Director of the United States Patent and Trademark Office